(12) United States Patent
Banks

(10) Patent No.: US 9,255,941 B1
(45) Date of Patent: Feb. 9, 2016

(54) SYSTEM AND METHOD FOR DETERMINING FLUENCE OF A SUBSTANCE

(75) Inventor: Bruce A Banks, Olmsted Township, OH (US)

(73) Assignee: The United States of America as Represented by the Administrator of National Aeronautics and Space Administration, Washington, DC (US)

( * ) Notice: Subject to any disclaimer, the term of this patent is extended or adjusted under 35 U.S.C. 154(b) by 585 days.

(21) Appl. No.: 13/112,293

(22) Filed: May 20, 2011

Related U.S. Application Data (60) Provisional application No. 61/349,386, filed on May 28, 2010.

(51) Int. Cl.
| | |
|---|---|
| *G01B 11/16* | (2006.01) |
| *G01P 5/04* | (2006.01) |
| *G01P 13/00* | (2006.01) |
| *G01N 19/08* | (2006.01) |
| *G01N 21/85* | (2006.01) |
| *G01B 13/24* | (2006.01) |

(52) U.S. Cl.
CPC .............. *G01P 13/0013* (2013.01); *G01B 11/16* (2013.01); *G01B 13/24* (2013.01); *G01N 19/08* (2013.01); *G01N 2021/8578* (2013.01); *G01P 5/04* (2013.01)

(58) Field of Classification Search
USPC .................... 356/35, 237.6, 431, 638, 621
See application file for complete search history.

(56) References Cited

U.S. PATENT DOCUMENTS

| | | | | |
|---|---|---|---|---|
| 5,350,899 | A * | 9/1994 | Ishikawa et al. | 219/494 |
| 6,525,334 | B1 * | 2/2003 | Brackett | 250/573 |
| 8,049,878 | B2 * | 11/2011 | Zoeller, III | 356/237.6 |

* cited by examiner

*Primary Examiner* — Gregory J Toatley
*Assistant Examiner* — Rebecca C Bryant
(74) *Attorney, Agent, or Firm* — Robert H. Earp, III (57) ABSTRACT

A system and method for measuring a fluence of gas are disclosed. The system has a first light detector capable of outputting an electrical signal based on an amount of light received. A barrier is positionable adjacent the first light detector and is susceptible to a change in dimension from the fluence of the gas. The barrier permits a portion of light from being received by the first light detector. The change in the dimension of the barrier changes the electrical signal output from the first light detector. A second light detector is positionable to receive light representative of the first light detector without the barrier. The system and method have broad application to detect fluence of gas that may cause erosion chemical reaction causing erosive deterioration. One application is in low orbit Earth for detecting the fluence of atomic oxygen.

19 Claims, 7 Drawing Sheets

SYSTEM AND METHOD FOR DETERMINING FLUENCE OF A SUBSTANCE

CROSS REFERENCE TO RELATED APPLICATION

This application claims the benefit from U.S. Provisional Application No. 61/349,386, entitled "Materials International Space Station Expirement-6 (MISSE-6) Atomic Oxygen Fluence Monitor Experiment" filed on May 28, 2010, incorporated by reference herein in its entirety.

ORIGIN OF THE INVENTION

The invention described herein was made by an employee of the United States Government and may be manufactured and used by or for the Government for Government purposes without the payment of any royalties thereon or therefore.

BACKGROUND OF DISCLOSURE

The present invention generally relates to determining and/or monitoring fluence of a substance, such as a gas. The substance may cause chemical reactions resulting in erosion or other detrimental effects. In an embodiment, the present disclosure sets forth a system and method for monitoring fluence of a gas that may generally cause erosion.

Determining erosion and monitoring the amount of erosion is important, as erosion reduces the life of a structure. Erosion cause by chemical reacting and subsequent vaporization of reaction products may result in pitting, thinning, cracking or otherwise weakening the structure. Monitoring erosion may be difficult depending on the material and the environment. While a direct measurement of the amount of erosion on the structure itself may be preferred, it may be burdensome, costly or difficult to access the structure and determine the actual erosion. For many structures, only one side or portion of the structure may be accessible without removing the structure from service or removing other components of the structure in order to access the other side or portion. In addition, there are numerous environments that render direct measurements extremely difficult, if not impossible. For example, walls of radioactive containers present environmental, safety and logistical obstacles that render direct measurements impractical.

Another method of measuring erosion may be to position a similar material on the structure that can be removed and analyzed at a later date. The material may be inspected weighed and its properties may be compared to pre-service properties. While such an approach may improve access, it still requires removing and analyzing prior to making any determination of erosion. Such an approach is costly and provides no early indication of erosion until the material is retrieved and inspected.

Electrical resistance and linear polarization resistance probes rely on electrical current being transmitted through a surrogate material and measuring changes in the resistance of the electrical circuit as the material degrades or corrodes. For example, as the material disintegrates resistance increases. Measuring the resistance provides an indication of the amount and level of corrosion.

However, in some instances, the combination of environmental obstacles, safety issues, and lack of access, prevent the use of any of these erosion-monitoring techniques. For example, structures in low orbit earth are not only difficult to access but present unique environmental issues, safety issues, and changing environmental conditions, such as temperature, solar exposure, and atomic oxygen flux. Therefore, there exists a need for a new system and method for determining erosion and/or monitoring fluence of a substance that may cause erosion or other detrimental effects.

SUMMARY OF INVENTION

In an embodiment, a system for measuring a fluence of a reactive gas is disclosed.

A system for measuring a fluence of gas has a first light detector outputting an electrical signal based on an amount of light received. A barrier is positioned adjacent the first light detector and is susceptible to a change in dimension from the fluence of the gas. The barrier prevents a portion of light from being received by the first light detector. A change in the dimension of the barrier changes the electrical signal output from the first light detector. A second light detector is positioned to receive light representative of the first light detector without the barrier.

In another embodiment, a method of measuring a fluence of a gas is provided. The method involves positioning a first light detector to receive light. The method prevents a portion of light from being received at the first light detector using a barrier having a gap between a first portion and a second portion. Only light passing through the gap reaches the first light detector. The method compares light received from the first light detector to light received from the second light detector to determine erosion of the barrier.

In yet another embodiment, a method of measuring a fluence of a gas having a first photodiode outputting a current based on intensity of light received is disclosed. A barrier is positioned to block a portion of light received at the first photodiode. The barrier has a first portion and a second portion separated by a gap such that only light passing through the gap is received at the first photodiode. A second photodiode is positioned away from the barrier such that the second photodiode receives light representative of the first photodiode without the barrier.

DETAILED DESCRIPTION

It is to be understood that the following disclosure provides different embodiments, or examples, for implementing different features of various embodiments. Specific examples of components, arrangements or methods of using these are described to simplify the disclosure. While specific embodiments, specific implementations and specific uses are disclosed, none of these should be taken as limiting the present invention to only those specific embodiments, implementations or uses. The present disclosure should be interpreted to broadly support the claims and should only be limited by the claims. In addition, the present disclosure may repeat reference numerals and/or letters in the various examples. This repetition is for the purpose of simplicity and clarity and does not in itself dictate a relationship between the various embodiments and/or configurations discussed.

The present disclosure sets forth a system and method for measuring fluence of a substance, such as a gas. The system and the method may be used in numerous fields of endeavors for monitoring fluence of the substance. For example, it may be advantageous to monitor and/or detect a substance that causes erosion or deterioration. While the present disclosure sets forth monitoring and/or determining fluence of a gas, such as atomic oxygen, the present disclosure is applicable to any substance in which monitoring or detecting of the substance and/or its erosion may be used. As an example, any gas that may cause erosion may be monitored with one or more embodiments of the present disclosure. Again, specific embodiments related to monitoring atomic oxygen and/or using of the system and method in low orbit Earth should be taken for explanatory purposes only and should not be deemed to limit the invention.

Figure 1A:
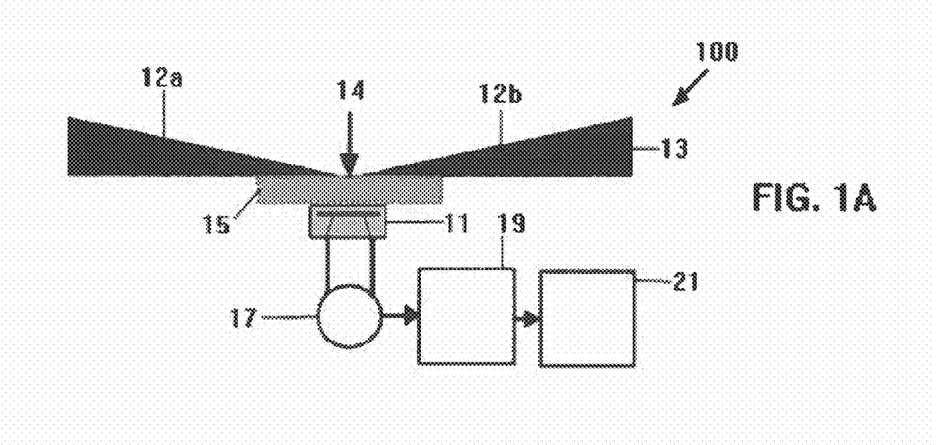
FIG. 1A illustrates a system utilizing a first light detector having a barrier in an embodiment of the present invention.
Figure 1B:
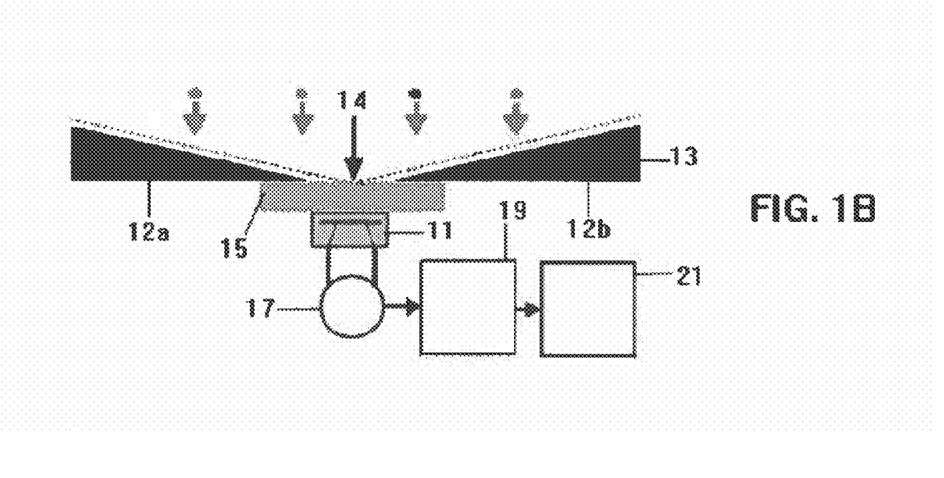
FIG. 1B illustrates a system utilizing a first light detector having a barrier eroded by a substance in an embodiment of the present invention.

An embodiment of a system 100 for measuring a fluence of a substance is generally shown in FIGS. 1A and 1B. The system 100 may comprise a first light detector 11 capable of receiving, sensing, monitoring and/or determining an amount of light received. Non-limiting examples of the first light detector 11 include but are not limited to a photodiode, a photocell, a solar cell, a phototransistor or any device capable of outputting a current, a voltage, or a signal representative of an amount of light received. The first light detector 11 may be generally referred to as the first photodiode 11 to explain one or more embodiments of the disclosure, but it should be understood that the disclosure should not be limited to a photodiode and other light detectors described herein or known to those having ordinary skill in the art to may be implemented within the spirit of the invention.

The first light detector 11 may output a signal, such as an electrical signal, upon receiving light, and the signal may be based on an amount of the light. In an embodiment, the first light detector 11 may output a current based on the amount of the light received by the first light detector 11. The current may be based on and/or representative of the amount of the light received at the first light detector 11. For example, the first light detector 11 may convert light energy received to free electrons.

A window 15 may be positioned between the light source and the first light detector 11. Light received by the first light detector 11 may be passed through the window 15. The window 15 may be a fused silica and grit blasted. In an embodiment, the window 15 diffusely scatters the light before being received by the first light detector 11.

A barrier 13 may be positioned adjacent the first light detector 11. Preferably, the barrier 13 is positioned between the first light detector 11 and the light source. The barrier 13 may block or otherwise prevent a portion of light transmitted from the light source from being received by the first light detector 11. A portion of the light transmitted from the light source may pass through the barrier 13 to the first light detector 11.

The barrier 13 may be chosen for its known relationship with the substance. For example, it may be known that at a given flux of the gas, the barrier 13 may erode at a predetermined rate. The barrier 12 may be made of a material substantially similar or identical to a material of a corrosive susceptible component. As an example, it may be desirable to monitor and predict when a component may fail by erosion, deterioration that causes erosion or other damage which removes material from the substance. However, there are many reasons in which the erosion of the component itself may not be measurable, such as limited access, safety concerns, environmental issues or the like. Accordingly, the system 100, as shown in FIGS. 1A and 1B, may be used, and the barrier 13 may be chosen with a similar or substantially similar material to the component. In an embodiment, the barrier 13 may be made of graphite, such as pyrolytic graphite. Of course, graphite is merely used as an example as it reacts with atomic oxygen which is an example of the substance, but a person having ordinary skill in the art will appreciate that the barrier 13 may be made of any material necessary to measure, determine and/or monitor fluence of a given substance.

In an embodiment, the barrier 13 may comprise a first portion 12a and a second portion 12b. The first portion 12a may be positioned at a distance from the second portion 12b to create a gap 14 in the barrier 13. The gap 14 may have a predetermined size and/or shape to permit a portion of light from the light source to contact the first light detector 11 and prevent the remaining portion of light from being received by the first light detector 11. In an embodiment, the gap 14 may be relatively small so as to only permit a very small portion of light from being received by the first light detector 11.

Figure 3A:
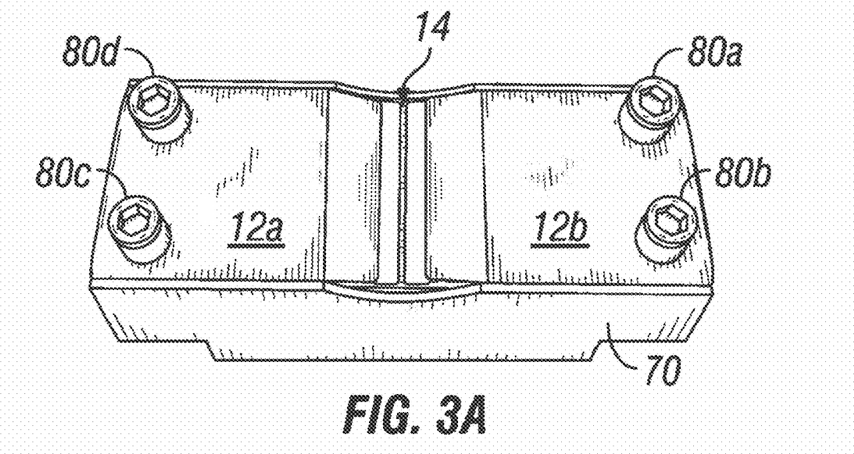
FIG. 3A illustrates a perspective view of a barrier secured to a housing in an embodiment of the present invention.

FIG. 3A illustrates an embodiment of the first portion 12a and the second portion 12b secured to a housing 70. The gap 14 is formed between the first portion 12a and the second portion 12b. Bolts 80a and 80b secure the second portion 12b to the housing 70. Bolts 80c and 80d secure the first portion 12a to the housing 70. Securing the portions 12a, 12b prevents axial or lateral movement and, thus, prevents changes in the size of the gap 14 from that movement. The present disclosure should not be deemed as limited to using bolts to secure the portions 12a, 12b and/or the use of the housing 70.

The barrier 13 may be susceptible to a change in dimension from fluence of a substance, such as a corrosive substance. The change in dimension of the barrier 13 may be due to chemical reaction causing volatile reaction products to result in erosion. Specifically, in an embodiment where the substance is a gas, the gas may interact with the barrier 13 to change the dimension of the barrier 13, such as by corroding the barrier 13. As the substance contacts and/or reacts with the barrier 13, dimensions of the barrier 13 may be changed causing a size, such as a width of the gap 14 to increase or decrease. The change in the size of the gap 14 changes an amount of the first light detector 11 exposed to the light source. As a result, for a given amount of light from the light source, increasing the size of the gap 14 will increase the amount of light received by the first light detector 11. The fluence of the reacting substance on the barrier 13 may be related to the change in the size of the gap 14. For example, as the fluence of the substance increases, then the size of the gap 14 may increase. FIG. 1B illustrates the size of the gap 14 increases due to oxidation or corrosion of the barrier 13.

Figure 2:
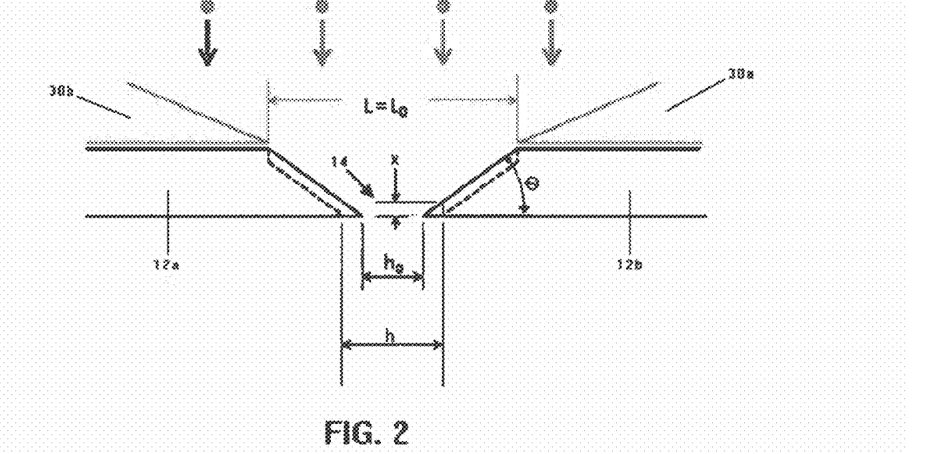
FIG. 2 illustrates a schematic of a barrier prior to and after erosion in an embodiment of the present invention.

FIG. 2 illustrates a schematic of the barrier 13. As shown in FIG. 2, the first portion 12a and the second portion 12b each may be wedge shaped and have an angle of inclination, θ, preferably less than ninety degrees. In an embodiment, the angle of inclination is less than twenty-five degrees, and may even be less than fifteen degrees. In a specific example, the angle of inclination θ is about twelve degrees. The initial size of the gap 14 prior to erosion, such as in FIG. 1A is shown as, $h_0$, in FIG. 2. The size of the gap 14 increases due to the erosion, such as shown in FIG. 1B and is represented in FIG. 2 as h. A vertical depth of the erosion is shown as X in FIG. 2. A non-corrosive layer 30a, 30b may be positioned on the first portion 12a and the second portion 12b. The non-corrosive layer 30a, 30b may be made of a substance that is not susceptible to erosion, corrosion or deterioration, or at least less susceptible than the portions 12a, 12b. In an embodiment, the non-corrosive layers 30a, 30b may be made of aluminum which may be much more resistant to atomic oxygen than graphite.

The fluence of the substance may be given by equations 1 and 2:

$$F = X/E \quad (1)$$

$$F = (h - h_0)(\tan \theta)/2E \quad (2)$$

"F" is the flux of the substance. "X" is the erosion depth of the barrier 13 as described above. "h" and "$h_0$" are the gap sizes, such as widths as shown in FIG. 2. "E" is a constant depending on the substance and the material of the barrier 13. For example, in an embodiment where the barrier 13 is graphite and the substance is atomic oxygen, E may be $4.15 \times 10^{-25}$ cm³/atom.

The first light detector 11 may be connected to a measuring device 17 that may detect and/or measure the signal outputted from the first light detector 11. In an example, the first light detector 11 outputs a current based on an amount of light received, and the measuring device 17 may detect and/or determine the current. In an embodiment, the measuring device 17 may be a current or voltage measuring circuit 17.

An amplifier 19 may be in communication with the measuring circuit 17 as shown in FIGS. 1A and 1B to amplify the signal output from the first light detector 11 and/or the measuring circuit 17. In an example where the first light detector 11 outputs a current, the amplifier 19 may be an operational amplifier that produces a current or voltage substantially higher than the current generated from the first light detector 11. For example, the amplifier 19 may amplify the current or voltage by at least one hundred times the voltage or amperes generated by the first light detector 11.

The amplifier 19, the measuring device 17 and/or the first light detector 11 may be in communication with a data logger 21 that may comprise a data storage device, such as memory, and/or a processor. The data logger 17 may store information or data related to the amount of light received by the first light detector 11. For example, the data logger 17 may store information related to an amount of current or voltage output from the first light detector 11. The data logger 17 may store the time each current or voltage was received by the data logger 17 and/or generated by the first light detector 11.

Figure 3B:
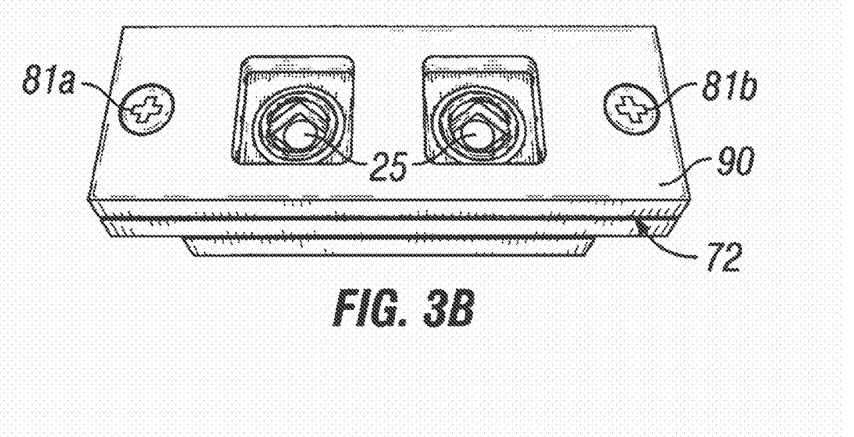
FIG. 3B illustrates a perspective view of a second light detector secured to a housing in an embodiment of the present invention. Note: This second light detector can be identical to the 3A configuration, including using a single gap between portions 12a and 12b with the exception of not having graphite wedges.
Figure 4:
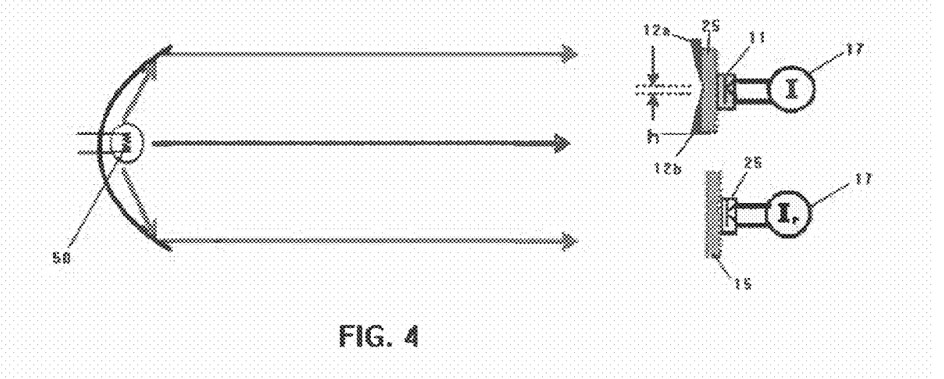
FIG. 4 illustrates a light source directing light to a first light detector and a second light detector in an embodiment of the present invention.

Advantageously, the system 100 may utilize a second light detector 25 as shown in FIGS. 3B and 4. The second light detector 25 may be a photodiode, a photocell, a solar cell, a phototransistor or any device capable of detecting light and outputting a signal representative of an amount of light received. For example, in FIG. 12 the second light detector 25 may be any device that outputs an electrical signal, such as a current or a voltage, based on an amount of light received.

FIG. 4 illustrates an embodiment where the second light detector where the photodiode is on the right side.

FIG. 3B illustrates the second light detector secured to a housing 72. For example, the housing 72 may have a top plate 90 secured to the housing 72 via screws 81a, 81b. It should be noted that FIGS. 3A and 3B are merely embodiments of the light detectors 11, 25 with housings 70, 72. The actual structure surrounding the light detectors 11, 25 may be substantially different based on the substance, the component in which corrosion measuring is to be used and/or other considerations that will be appreciated by those having ordinary skill in the art.

The light impinging upon the second light detector may come from any source, such as the Sun, a light emitting diode, a laser, or any form of light capable of transferring energy to the first light detector 11 and the second light detector 25. The second light detector 25 may utilize one or more of the components of the system 100 illustrated in FIGS. 1A and 1B. For example, the window 15 may be positioned between the second light detector 25 and the light source 50. The second light detector 25 may be in communication with the amplifier 19, the measuring device 17 and/or the data logger 21. It should be noted that the second light detector 25 may be in communication with the same amplifier, measuring device and data logger or may have separate components that function similarly as those used with the first light detector 11. In an embodiment where the first light detector 11 and the second light detector 25 have a separate measuring device 17, amplifier 19 and/or data logger 21, one or more of these components may be in communication with each other. For example, the data logger 21 of the first light detector 11 may be in communication with the data logger 21 of the second light detector 25.

The second light detector 25 may be positioned adjacent the first light detector 11. The second light detector 25 may be positioned away from the barrier 13 such that the second light detector 25 receives an amount of light from the light source 50, shown in FIG. 4, which is substantially similar to the amount of light the first light detector 11 would receive without the barrier 13. As an example, the barrier 13 of the first light detector 11 blocks a portion of a total amount of light, and the second light detector 25 receives the total amount of light. Accordingly, as long as light is transmitted from the light source 50, the amount of light received at the first light detector 11 may be compared to the amount of light received at the second light detector 25. The comparison may determine the size of the gap 14 and, in turn, an amount of fluence of the substance on the barrier 13. In an embodiment, the data logger 21 may store data related to outputs of the first light detector 11 and the second light detector 25. In addition, the data logger 21 may process the data to determine a relationship between the outputs of the light detectors 11, 25, such as currents, which may be used to determine a size of the gap 14 and/or a fluence of the substance on the barrier 13.

Figure 5:
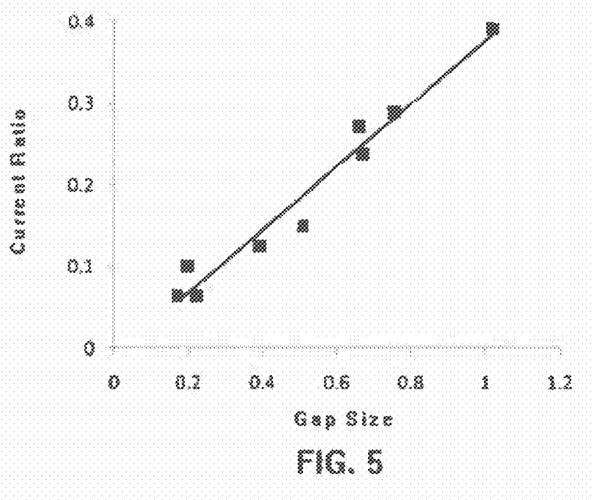
FIG. 5 illustrates a graph showing a relationship between size of a gap between portions of a barrier and current output from the first and second light detector.

FIG. 5 illustrates a graph showing a relationship of size of the gap 14 on the x-axis to a ratio of current output from the first light detector 11 to current output by the second light detector 25. As shown, the relationship may be a substantially linear relationship.

One use of the system 100 is in low Earth orbit on a satellite, such as International Space Station, where the Sun may be the light source. In such a use, the light received at the first light detector 11 is not constant and fluctuates with as the first light detector 11 moves with respect to the Sun and/or the Earth moves with respect to the first light detector 11. In such an environment, atomic oxygen is an erosive substance that requires monitoring on components.

The ability to measure the atomic oxygen fluence as a function of time as atomic oxygen impinges upon a spacecraft surface, for example, in low Earth orbit has been difficult to achieve. Early devices to measure atomic oxygen fluence consisted of thin films of silver or carbon coatings (often called them film actinometers) whose electrical resistivity increased with time as the silver oxidized or the carbon was converted to gaseous oxides. However, thin film devices have limited fluence measurement capability due to the finite thickness of the thin films and provide nonlinear responses as a function of fluence.

The time variation of accumulation of atomic oxygen fluence is also difficult to predict based on end point Kapton H weight loss measurements as a result of variations in solar activity, spacecraft altitude, and spacecraft orientation. The prediction of atomic oxygen fluence from orbital and spacecraft orientation data is also complicated by potential shielding of the ram facing surfaces. This is especially true for complex distributed space structures such as the International Space Station.

In an embodiment, the system 100 may be used as an atomic oxygen fluence monitor that is based on the erosion of the barrier 13. The barrier 13 may comprise two portions 12a, 12b, each having an inclined surface, as described above. The barrier 13 may be made of a substance that reacts with the atomic oxygen, such as pyrolytic graphite. The angle of the portions 12a, 12b may be formed by any known technique for forming an angle of an environmentally erosive substance. For example, the barrier 13 may be secured or attached to another material and sanded with abrasive sand paper over a flat surface. In the case of pyrolytic graphite, aluminum may be attached to the graphite to aid in sanding the graphite with abrasive paper. It may be advantageous to form the angled wedges of the barrier 13 without forming irregular sharpened ends. To minimize the consequences of imperfections in using the abrasive process to form the portions 12a, 12b, an additional sharpening step may be performed. One such example is using a hyperthermal atomic oxygen beam from an end Hall atomic oxygen source, which may operate on pure oxygen to produce 70 eV diatomic oxygen ions which upon impact dissociate into atomic oxygen thus causing oxidation and subsequent erosion.

The portions 12a, 12b of the barrier 13 may be positioned such that a predetermined gap 14 exists between the portions 12a, 12b of the barrier 13. For example, an initial size of the gap 14 may be a small, such as less than one tenth of a centimeter, for example 0.0578 centimeters. In this embodiment, the light detectors 11, 25 are photodiodes outputting current based on an amount of light received from the Sun. To be able to discriminate between changes in the current due to Sun angle variations and changes due to erosion of the portions 12a, 12b, the second photodiode 25 may be used that has a view of the Sun incidence upon the first photodiode 11. The current from the first photodiode 11 may be compared with the second photodiode 25.

Advantageously, a substantially linear relationship exists between current output from the first photodiode 11 and accumulated fluence of the atomic oxygen. As a result, the system 100 is capable of measuring high fluence. Validation of this result was confirmed by experiment where the light source 50, shown in FIG. 4, was a lamp positioned a large distance from the light detectors 11, 25. The gap 14 between the portions 12a, 12b of the barrier 13 was manually widened to allow measurement of the ratio of the current from the first light detector 11, "I", to the current output from the second light detector 25, "$I_R$," as a function of size of the gap 14, which is referred to as h in FIG. 2. As shown in FIG. 5, the system 100 has a reasonably linear response with a correlation coefficient of 0.963 over a fluence range which represents at least $3.14 \times 10^{22}$ atoms/cm$^2$ based on the erosion yield of $4.15 \times 10^{-25}$ cm$^3$/atoms. Specifically, the linear relationship shown is a plot of size of the gap 14 versus a ratio of current of the first photodiode 11 with respect to the current of the second photodiode 25. The scatter in the data points is thought to be due to the uncertainty in the setting and measurement of the size of the gap 14 between the portions 12a, 12b.

Figure 6:
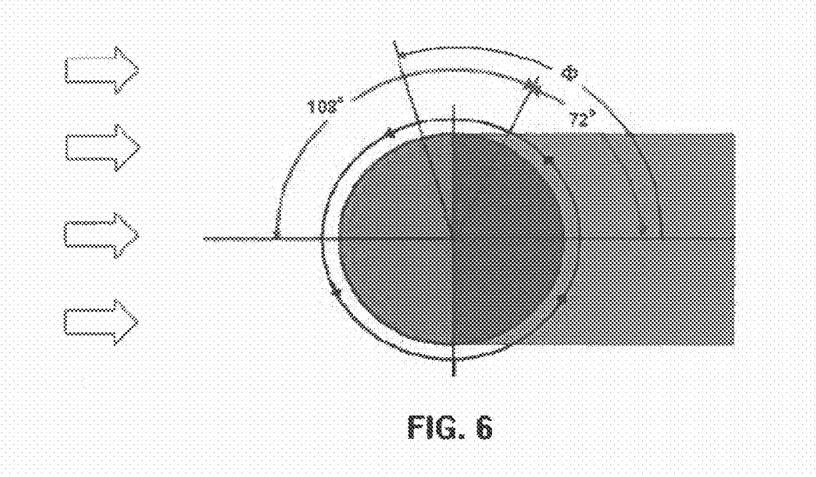
FIG. 6 is an illustration of a measurement domain of a system for measuring corrosion used in low Earth orbit.

For this explanatory use, measurements of the current of the photodiodes 11, 25 were recorded on a time interval of every 108 minutes. The time interval between successive data points was purposely chosen to be slightly out of phase with the 91.2 minute average orbital period to insure that near normal solar illumination on the photodiodes 11, 25, which were oriented with their surface normal vectors facing tangential to the Earth's surface and facing the ram direction would frequently occur. See FIG. 6 as an example where Φ is 90 degrees.

The data for near normal illumination could be corrected based on off-normal to normal short circuit current calibrations for the first photodiode 11 and the second photodiode 25. The laboratory calibration data for the ratio of measured to theoretical (based on sin Φ) currents for the photodiodes 11, 25 is shown in FIGS. 7 and 8.

As expected, the calibration data shows a quicker loss in current in the first photodiode 11 with time after 6 am due to the fact that the active surface of the first photodiode 11 is recessed within the housing 70 in the embodiment of FIG. 3A. As a result, Sun light may begin to miss the active surface of the first photodiode 11 after 30 minutes past midnight, when the Sun is beginning to have an inclined angle of arrival on the first and second photodiodes 11, 25. The window 15 adjacent the first photodiode 11 is sandblasted to moderate the effect of off-normal illumination beginning to miss the active surface of the first photodiode 11. The window 15 may be grit blasted to diffusely scatter the sunlight which then impinges upon the first photodiode 11. The second photodiode 25 may have similar output losses with off-normal illuminations as the first photodiode 11 and for the same reasons.

Figure 7:
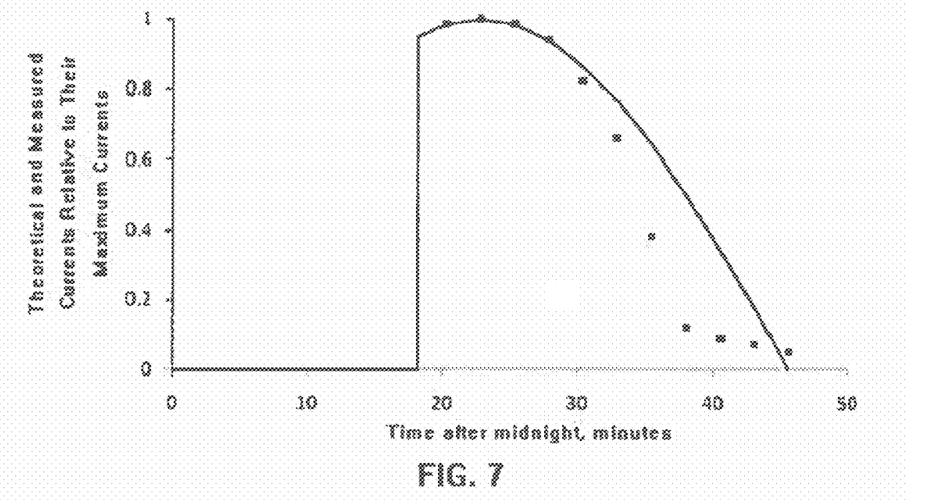
FIG. 7 illustrates a graph of time with respect to a ratio of current output from a first light detector and current output from a second light detector.
Figure 8:
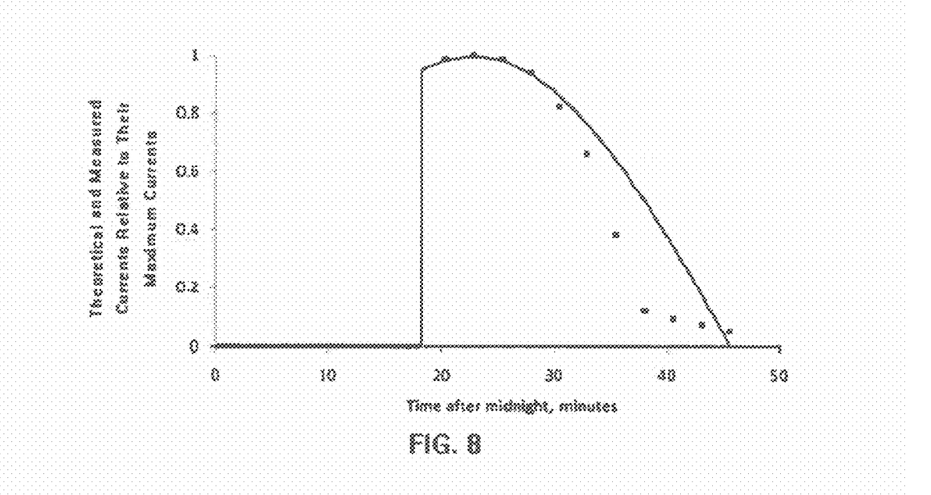
FIG. 8 illustrates a normalized graph of time with respect to a ratio of current output from a first light detector and current output from a second light detector.
Figure 9A:
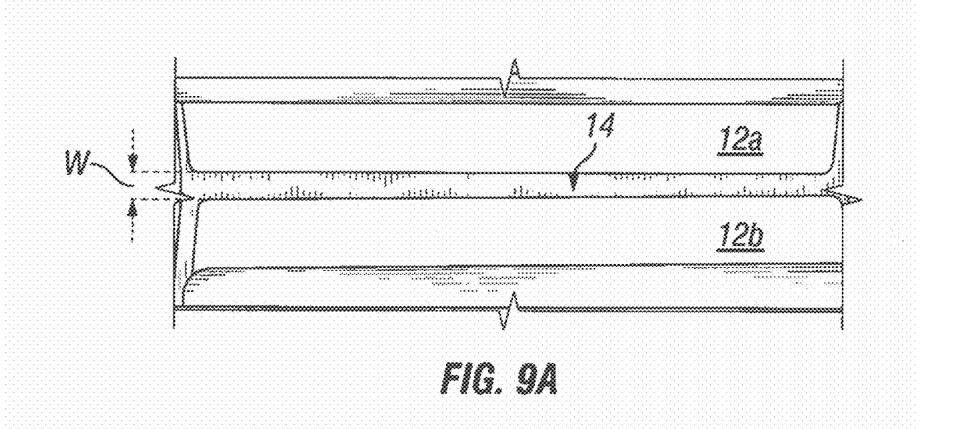
FIG. 9A is a pictorial representation of a gap of a barrier prior to erosion in an embodiment of the present invention.
Figure 9B:
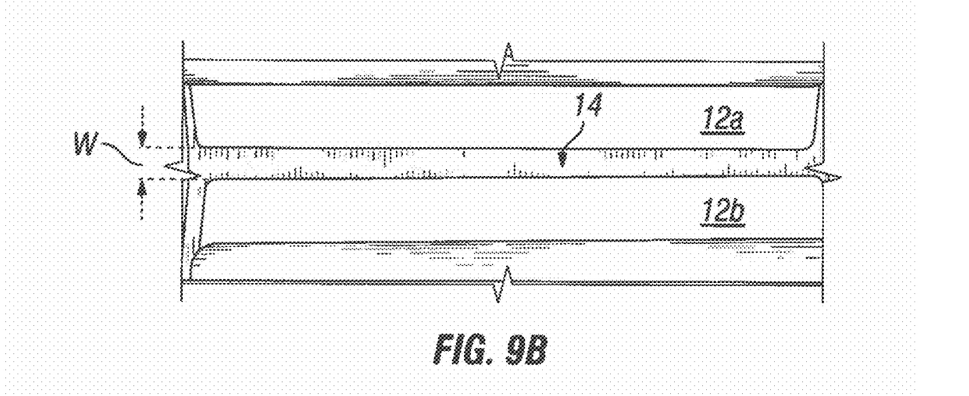
FIG. 9B is a pictorial representation of a gap of a barrier after erosion from the substance in an embodiment of the present invention.

Using data from FIGS. 7 and 8, one can determine that data points taken between 20.3 and 25.3 minutes after midnight could be easily adjusted for off-normal output calibrations to be able to make a long term plot of maximum current versus time to produce atomic oxygen fluence data as a function of time. FIGS. 9A and 9B illustrate an increase in the size of the gap 14 due to erosion caused by atomic oxygen reacting with the barrier 13, specifically the portions 12a, 12b. As shown, the size of the gap 14 in FIG. 9B is significantly greater than the size of the gap 14 shown prior to use on the International Space Station and prior to erosion due to atomic oxygen.

Figure 10:
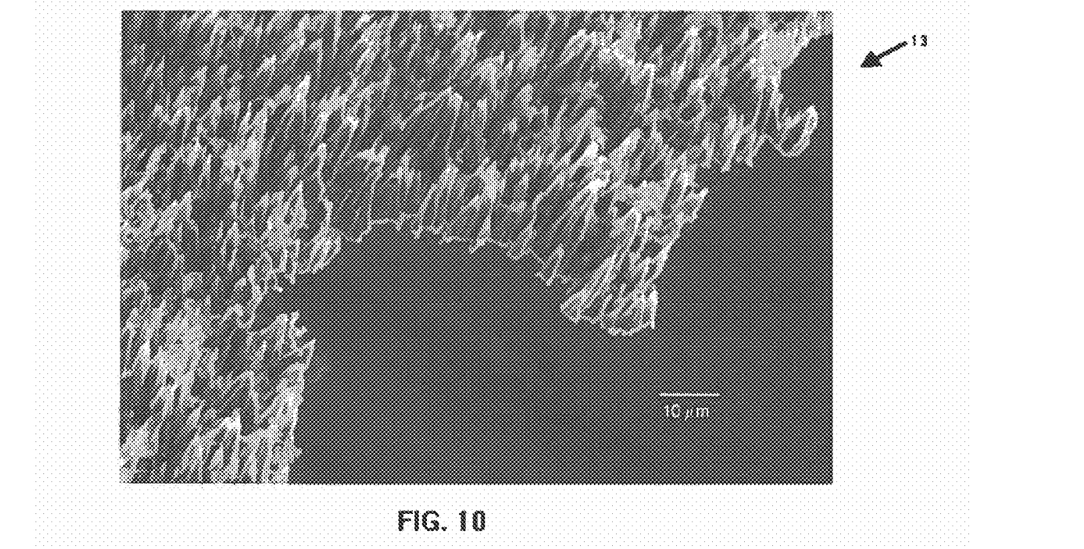
FIG. 10 illustrates a scanned electron microscope image of a barrier after erosion in an embodiment of the present invention.
Figure 11:
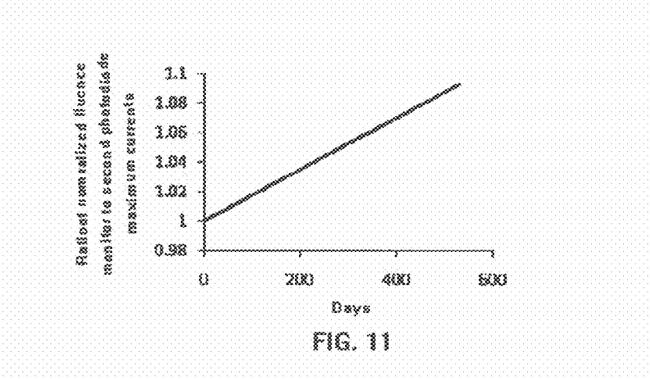
FIG. 11 illustrates a graph of time with respect to expected ratio of normalized current output from a first light detector to a second light detector.

Although the embodiment of the portions 12a, 12b of FIG. 3A have substantially straight edges on a macroscopic scale, the edges may be irregular on a microscopic scale. However, the portions 12a, 12b may continue to retain a tapered sharp edge which is limited in sharpness only by the microscopic cone-to-valley texture on the pyrolytic graphite that is the result of atomic oxygen erosion, as shown in FIG. 10. Assuming a linear growth in accumulated atomic oxygen fluence with time, one would expect a resulting fluence versus time plot as shown in FIG. 11.

In summary, the specific use of the system 100 on the International Space station permitted atomic oxygen to erode the portions 12a, 12b of the barrier 13 that partially cover the first light detector 11. As the portions 12a, 12b erode, the area of the first light detector 11 that is illuminated by the Sun increases. The current output from the first light detector 11, which is proportional to the area of illumination, was measured and recorded as a function of time. The current output from a second light detector 25 without the barrier 13 was oriented in the same direction with respect to the Sun and was also recorded with respect to time. The second light detector 25 had an unobstructed view of the Sun. The ratios of the currents from the light detectors 11, 25 have a linear relationship with the accumulated atomic oxygen fluence and are independent of the intensity of solar illumination. Ground hyperthermal atomic oxygen exposures facilities were used to evaluate the linearity of the ratio of the currents to the atomic oxygen fluence indicated that the system 100 was linear and capable of measuring atomic oxygen fluence up to at least $3.14 \times 10^{22}$ atoms/cm$^2$.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

The invention claimed is:

1. A system for measuring atomic oxygen fluence comprising:
a first light detector outputting an electrical signal based on an amount of light received;
a barrier positioned adjacent the first light detector and susceptible to a change in dimension from the fluence of atomic oxygen, the barrier preventing a portion of light from being received by the first light detector wherein the change in the dimension of the barrier changes the electrical signal output from the first light detector;
a second light detector positioned to receive light representative of the first light detector without the barrier; and
a processor capable of determining the fluence of atomic oxygen based on the comparison of the light received from the first light detector and the second light detector, wherein the system measures atomic oxygen fluence.

2. The system of claim 1 wherein at least one of the first light detector and the second light detector is a photodiode.

3. The system of claim 1 wherein the first light detector and the second light detector output a current based on an amount of light received.

4. The system of claim 1 wherein the barrier comprises two portions separated by a gap and further wherein the gap is positioned such that only light passing through the gap is received by the first light detector.

5. The system of claim 4 wherein the gap increases in size due to erosion or deterioration causing erosion from the gas.

6. The system of claim 4 further comprising a processor in communication with the first light detector and the second light detector determining a size of the gap based on a ratio of light received from the first light detector and the second light detector.

7. The system of claim 1 wherein the first light detector and the second light detector output current or voltage based on light received from the Sun.

8. The system of claim 1 wherein the electrical signal is electrical current and further wherein the second light detector outputs current based on the amount of light received.

9. The system of claim 8 wherein a relationship between the current output from the first light detector and the current output from the second light detector relates to the fluence of atomic oxygen.

10. A method of measuring atomic oxygen fluence comprising:
positioning a first and second light detector to receive light;
preventing a portion of light from being received at the first light detector using a barrier having a gap between a first portion and a second portion, wherein only light passing through the gap reaches the first light detector;
comparing light received from the first light detector to light received from the second light detector to determine erosion or corrosion of the barrier, wherein the method measures atomic oxygen fluence; and
determining the fluence of atomic oxygen based on the comparison of the light received from the first light detector and the second light detector.

11. The method of claim 10 further comprising outputting a first amount of current from the first light detector based on light received at the first light detector; and outputting a second amount of current from the second light detector based on light received at the second light detector.

12. The method of claim 11 further comprising comparing the first amount of current to the second amount of current to determine the fluence of atomic oxygen on the barrier.

13. The method of claim 11 further comprising comparing the first amount of current to the second amount of current to determine a size of the gap.

14. The method of claim 10 wherein the fluence of atomic oxygen is determined independent with respect to intensity of the light.

15. The method of claim 10 wherein the barrier is made of a substance that changes dimension upon the fluence of atomic oxygen.

16. A system for measuring fluence of atomic oxygen comprising:
a first photodiode outputting a current or a voltage based on light received;
a barrier positioned to block a portion of light received at the first photodiode, the barrier having a first portion and a second portion separated by a gap such that only light passing through the gap is received at the first photodiode;
a second photodiode positioned away from the barrier such that the second photodiode receives light representative of the first photodiode without the barrier, wherein the system measures atomic oxygen fluence; and
a processor capable of determining the fluence of atomic oxygen based on the comparison of the light received from the first light detector and the second light detector.

17. The system of claim 16 wherein the first photodiode and the second photodiode each generating a current based on an amount of the light received.

18. The system of claim 17 wherein a comparison of the first current and the second current relates to the fluence of atomic oxygen on the barrier.

19. The system of claim 16 wherein a ratio of the current of the photodiodes relates substantially linearly to a width of the gap.

* * * * *